(12) United States Patent
Clayton et al.

(10) Patent No.: US 7,138,471 B2
(45) Date of Patent: Nov. 21, 2006

(54) HYDROPHILIC BIOMEDICAL COMPOSITIONS

(75) Inventors: Anthony Brian Clayton, Oakleigh (AU); Timothy Charles Hughes, Ferntree Gully (AU); Peter Agapitos Kambouris, Box Hill North (AU); Gordon Francis Meijs, Murrumbeena (AU)

(73) Assignee: Commonwealth Scientific and Industrial Research Organisation, Canberra (AU)

( * ) Notice: Subject to any disclaimer, the term of this patent is extended or adjusted under 35 U.S.C. 154(b) by 312 days.

(21) Appl. No.: 10/897,302

(22) Filed: Jul. 22, 2004

(65) Prior Publication Data

US 2005/0004255 A1    Jan. 6, 2005

Related U.S. Application Data

(62) Division of application No. 10/048,312, filed as application No. PCT/AU00/00916 on Aug. 2, 2000, now Pat. No. 6,774,197.

(30) Foreign Application Priority Data

Aug. 2, 1999 (AU) .................................... PQ1977

(51) Int. Cl.
*C08F 212/00* (2006.01)
*A61F 2/16* (2006.01)

(52) U.S. Cl. ................... 526/307.5; 526/260; 526/266; 526/303.1; 526/310; 526/320; 526/347; 623/6.11

(58) Field of Classification Search ................ 526/260, 526/266, 303.1, 307.5, 310, 320, 347; 623/6.11
See application file for complete search history.

(56) References Cited

U.S. PATENT DOCUMENTS

| | | | |
|---|---|---|---|
| 4,777,217 A | 10/1988 | Rasmussen et al. | |
| 5,316,704 A | 5/1994 | Wang et al. | |
| 5,480,950 A | 1/1996 | Wang et al. | |
| 5,647,409 A | 7/1997 | Christ et al. | |
| 5,772,667 A | 6/1998 | Blake | |
| 5,814,680 A | 9/1998 | Imafuku et al. | |
| 5,821,306 A | 10/1998 | Hodd | |
| 5,849,841 A * | 12/1998 | Muhlebach et al. | .......... 525/59 |

FOREIGN PATENT DOCUMENTS

| | | |
|---|---|---|
| EP | 336762 | 10/1989 |
| EP | 0647143 | 1/1998 |
| JP | 2202-128829 | 5/2002 |
| WO | WO 96/24075 | 8/1996 |
| WO | WO 98/28026 | 7/1998 |
| WO | WO 99/47185 | 9/1999 |
| WO | WO 00/55214 | 9/2000 |
| WO | WO 01/81075 | 11/2001 |

OTHER PUBLICATIONS

Derwent Jpat Online Abstract No. 99-267075/23 JP 11 080274 A (Menicon Co. Ltd.) Mar. 26, 1999.
Kazuhiko et al, Abstract JP2002128829, Monomer, Polymer, and Ophthalmic Lens Using the Same, Published May 9, 2002.

* cited by examiner

*Primary Examiner*—Helen L. Pezzuto
(74) *Attorney, Agent, or Firm*—Andrus, Sceales, Starke & Sawall, LLP

(57) ABSTRACT

A hydrophilic ethylenically unsaturated macromonomer is disclosed that is prepared by the addition polymerization of addition polymerizable monomers that include monomers that have hydroxyl or amino functional groups, some of which may be subsequently reacted to provide (meth)acryl ethylenic unsaturation. The macromonomers may be used to form intraocular lenses in situ by polymerization of the macromonomers, and thus treat presbyopia.

20 Claims, No Drawings

HYDROPHILIC BIOMEDICAL COMPOSITIONS

CROSS-REFERENCE TO RELATED APPLICATIONS

This application is a Divisional application of U.S. patent application Ser. No. 10/048,312, filed May 31, 2002, now U.S. Pat. No. 6,774,197, which is in turn is the U.S. national stage application of International Application PCT/AU00/00916, filed Aug. 2, 2000, which international application was published on Feb. 8, 2001, as International Publication WO 01/08604 in the English language, which International Application claims priority from Australian Patent Application No. PQ 1977, filed Aug. 2, 1999.

TECHNICAL FIELD OF THE INVENTION

This invention relates to hydrophilic ethylenically unsaturated macromonomers that are suitable for use in biomedical applications.

BACKGROUND OF THE INVENTION

The use of polymeric prostheses and biomedical mouldings has grown rapidly in recent times. Such mouldings may be used for contact lenses or for specific ophthalmic purposes. For example, they may be used for intraocular lenses and eye bandages. They may also be used for surgical mouldings such as heart valves and artificial arteries. Other applications include wound dressings, biomedical adhesives and tissue scaffolds. Use in drug delivery is a further application.

Disease of the lens material of the eye is often in the form of cataracts. The ideal cataract procedure is considered to be one where the lens capsule bag is maintained with the cataractous lens material removed through a small opening in the capsule. The residual lens epithelial cells are removed chemically and/or with ultrasound or lasers. A biocompatible material with appropriate optical clarity, refractive index and mechanical properties is inserted into the capsular bag to restore the qualities of the crystalline lens.

There have been recent advances in methods of inserting intraocular lens. For example, U.S. Pat. No. 5,772,667 assigned to Pharmacia Lovision Inc, discloses a novel intraocular lens injector. This device compresses an intraocular lens by rolling the lens into a tight spiral. The device injects the compressed lens through a relatively small incision in the eye, approximately 2–3 millimetres in length, resulting from a phacoemulsification procedure. The intraocular lens is inserted into a receiving channel of the injector in an uncompressed state and is urged into a cylindrical passageway. As the intraocular lens advances into the cylindrical passageway, the lens will roll upon itself into a tightly rolled spiral within the confines of the cylindrical passageway. An insertion rod is inserted into an open end of the cylindrical passageway and advances the compressed lens down the passageway. As the lens exits the passageway and enters the eye, the lens will expand back to its uncompressed state.

To avoid the need for such injection devices, it has been proposed that intraocular lenses be formed in situ after being injected as a liquid flowable form into the lens capsule bag. However, while this concept is attractive in that smaller incisions would be required, it raises further difficulties in that further polymeric reactions are required to take place and these are required to be not harmful to the patient. It is also a requirement that the reaction can take place over a relatively short time under mild reaction conditions. A further requirement is that the reaction is not appreciably inhibited by oxygen. A still further requirement is that no byproducts or residues are produced that are leachable and which may have an adverse biological effect on the patient. It is desirable that the refractive index of the polymer composition for ophthalmic applications is close to 1.41 being the refractive index of the natural biological lens material.

Patent Application PCT/EP96/00246 in the name of AG Ciba-Geigy discloses water soluble cross-linkable polymers which may be crosslinked in solution to form moulded compositions. These compositions have particular application in contact lenses. The polymers are derivatives of polyvinyl alcohols. A portion of the hydroxyl groups are preferably reacted with 2-vinyl-4,4-dimethylazlactone to produce ethylenically unsaturated macromonomers.

SUMMARY OF THE INVENTION

This invention provides in one form a hydrophilic ethylenically unsaturated macromonomer comprising units of structure:

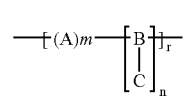

where:
m=an integer $\geq 1$
n=an integer $\geq 1$
r=an integer $\geq 1$

A is a non-reacted moiety resulting from the addition polymerisation of ethylenically unsaturated monomers.

B is a moiety resulting from the additional polymerisation of ethylenically unsaturated groups that possess hydroxyl or amino groups. Examples of suitable monomers are hydroxybutylacrylate and N hydroxy ethylacrylamide C has the following structure:

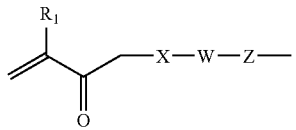

where:
$R_1$=H, Me
X=O, NH
Z=O, NH, NR, S, $CO_2$ where R is $C_1$–$C_8$ alkyl
W=linear, branched cyclic hydrocarbyl chains, polyether chains or heterochains, linear or cyclic.

It may include a mixture of moieties resulting from the use of a number of different ethylenically unsaturated monomers. The moieties are "non-reacted". By "non-reacted" we mean that under the reaction conditions that will allow appropriate side groups to be introduced into the copolymer backbone these "non-reacted" side groups will not form covalent bonds with other groups. Thus by this definition certain chemical groups may be included as being "non-reacted". The A moiety may be "non-reacted" in that under the reaction conditions side groups will not form covalent bonds. However, the A moiety may also be "non-reacted" because of the stoichiometry of the side groups. Thus it is possible for the A and B moieties to be the same and the A moiety remains unreacted because the number of equivalents of side groups is less than the equivalents of A and B. For example, A may include hydroxybutylacrylate and B may also be hydroxybutylacrylate.

The balance of the addition copolymer backbone, namely that part of the composition consisting of A and B moieties may be a random or block copolymer.

Examples of W are polyethylene glycol, polyethylene, cyclic and heterocyclic species such as phenyl rings or piperidine or mixtures of hydrophilic or hydrophobic polymers prepared by processes that allow control over end groups such as chain transfer chemistries and substituted variants thereof.

C may contain optional groups that are not ethylenically unsaturated polymerisable groups.

Preferably C is formed by suitable reaction of 2-vinyl-4, 4-dimethylazlactone, acryloyl or methacryloyl chloride or related compounds with the complimentary hydroxyl or amino groups on the copolymer backbone. Other methods include suitable reaction of isocyanatoethylmethacrylate, methacrylate anhydride, acrylate anhydride, active esters of acrylates or methacrylates. These can be prepared prior to reaction with the polymer or can be prepared in situ and attached to the copolymer by conventional coupling chemistries, for example the coupling of acrylic acid to alcohol groups on the backbone copolymer using carbodiimide chemistry.

The macromonomer is hydrophilic. By hydrophilic we mean the macromonomer may be diluted 10% w/w with water without affecting the visual clarity of the macromonomer when viewed through a 100 ml measuring cylinder.

In an alternative form this invention provides a method of treating presbyopia by removing a patient's lens from the lens capsule bag via an incision in the cornea, injecting into the lens capsule bag a macromonomer of Formula I and wherein the molecular weight of the macromonomer is in the range 10,000–300,000, and wherein the ethylenically unsaturated groups are provided by (meth)acrylamides, (meth)acrylate and styrenic moieties, and polymerising the macromonomer to a polymer having an E modulus in the range 0.01–100 kPa, preferably 0.1–10 kPa, and more preferably 0.5–5 kPa.

In a further alternative form this invention provides ethylenically unsaturated macromonomers comprising units of Formula I wherein the macromonomer or macromonomer solution has a viscosity at 25° C. in the range 1,000–20,000 cSt, and more preferably 1,000–10,000 cSt and after polymerisation to form biocompatible polymers having an E modulus in the range 0.01–100 kPa, preferably 0.1–10 kPa and more preferably 0.5–5 kPa.

In a still further embodiment this invention provides a method of preparing intraocular lenses in situ by injecting a flowable macromonomer composition of Formula I where the macromonomer composition has a viscosity at 25° C. in the range 1,000–20,000 cSt, more preferably 1,000–10,000 cSt and after polymerisation having to form a polymer having an E modulus in the range preferably 0.1–10 kPa and more preferably 0.5–5 kPa.

Preferably in the macromonomer the mole percentage of hydroxyl monomer is in the range 0.5–5% and more preferably 1.0–3.0%.

DETAILED DESCRIPTION OF THE INVENTION

The preferred scheme of reaction is set out below:

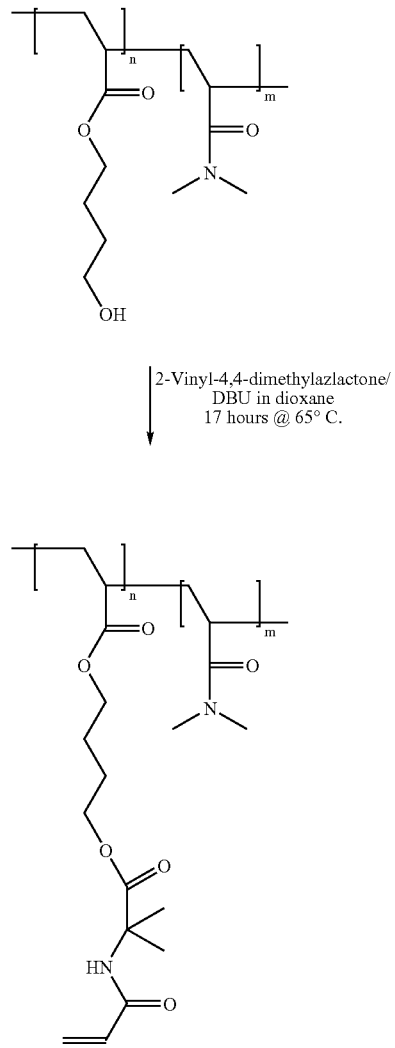

Acrylamide derivatives are preferred polymerisable groups as these tend to lead to less oxygen inhibition of the composition during crosslinking. This is particularly important for in situ crosslinking as is required when the preferred compositions are used as injectable intraocular compositions.

Crosslinked gels with different mechanical properties can be produced by irradiation of the macromonomer, depending on the degree of acrylamide functionalised and water content of the macromonomer formulation. The water content is preferably 10–70% w/w and more preferably 20–60%. The elasticity of the cured macromonomer is, as measured by the E modulus, in the range 0.01–100 kPa, preferably 0.1–10 kPa and more preferably 0.5–5 kPa. The E modulus is conveniently measured by equipment such as the Bohlin controlled stress rheometer.

This crosslinking has the advantage of being rapid and relatively insensitive to inhibition by oxygen.

The crosslinking process is therefore preferably carried out in such a way that the essentially aqueous solution of the water-soluble polymer comprising crosslinking groups is free or essentially free from undesired constituents, in particular from monomeric, oligomeric or polymeric starting compounds used for the preparation of the water-soluble, cross-linkable polymer, or from by-products formed during the preparation of the water-soluble, cross-linkable polymer, and/or that the solution is used without addition of a comonomer.

In the case of photo cross-linking, it is expedient to add an initiator which is capable of initiating free-radical crosslinking and is readily soluble in water. Examples thereof are known to the person skilled in the art; suitable photoinitiators which may be mentioned specifically are benzoins, such as benzoin, benzoin ethers, such as benzoin methyl ether, benzoin ethyl ether, benzoin isopropyl ether and benzoin phenyl ether, and benzoin acetate; acetophenones, such as acetophenone, 2,2-dimethoxyacetophenone and 1,1-dichloroacetophenone; camphorquinone; benzil, benzil ketals, such as benzil dimethyl ketal and benzil diethyl ketal, anthraquinones, such as 2-methylanthraquinone, 2-ethylanthraquinone, 2-tert-butylanthraquinone, 1-chloroanthraquinone and 2-amylanthraquinone; furthermore triphenylphosphine, benzoylphosphine oxides, for example 2,4,6-trimethylbenzoyl-diphenylphosphine oxide, benzophenones, such as benzophenone and 4,4'-bis(N,N-dimethylamino)benzophenone; thioxanthones and xanthones; acridine derivatives; phenazine derivatives; quinoxaline derivatives and 1-phenyl-1,2-propanedione 2-O-benzoyl oxime; 1-aminophenyl ketones and 1-hydroxyphenyl ketones, such as 1-hydroxycyclohexylphenyl ketone, phenyl 1-hydroxyisopropyl ketone, 4-isopropylphenyl 1-hydroxyisopropyl 1-hydroxyisopropyl ketone, 2-hydroxy-1-[-2(-hydroxyethoxy)phenyl]-2-methyl-propan-1-one, 1-phenyl-2-hydroxy-2-methylpropan-1-one, and 2,2-dimethoxy-1,2-diphenylethanone, all of which are known compounds.

Particularly suitable photoinitiators, which are usually used with UV lamps as light sources, are acetophenones, such as 2,2-dialkoxybenzophenones and hydroxyphenyl ketones, in particular the initiators known under the trade names IRGACURE®2959 and DAROCURE®1173.

Another class of photoinitiators usually employed when argon ion lasers are used are benzil ketals, for example benzil dimethyl ketal.

The photoinitiators are added in effective amounts, expediently in amounts of from about 0.3 to about 2.0% by weight, in particular from 0.3 to 0.5% by weight, based on the total amount of the water-soluble, cross-linkable polymer.

The water-soluble, cross-linkable polymers which are suitable in accordance with the invention can be crosslinked by irradiation with ionising or actinic radiation, for example electron beams, X-rays, UV or VIS light, ie electromagnetic radiation or particle radiation having a wavelength in the range from about 280 to 650 nm. Also suitable are UV lamps, He/De, argon ion or nitrogen or metal vapour or NdYAG laser beams with multiplied frequency. It is known to the person skilled in the art that each selected light source requires selection and, if necessary, sensitisation of the suitable photoinitiator. It has been recognised that in most cases the depth of penetration of the radiation into the water-soluble, cross-linkable polymer and the rate of curing are in direct correlation with the absorption coefficient and concentration of the photoinitiator.

If desired, the crosslinking can also be initiated thermally with an appropriate thermal free radical initiator, or by redox processes well known in the art. It should be emphasised that the crosslinking can take place in a very short time in accordance with the invention, for example, in less than five minutes, preferably in less than one minute, in particular in up to 30 seconds, particularly preferably as described in the examples.

In general hydrophilic copolymers are preferably prepared by standard free radical polymerisation of dimethyl acrylamide with the active hydrogen comonomer, hydroxy butyl acrylate or N-hydroxy ethyl acrylamide, in dioxane to afford white powdery polymers. The feed ratio of monomers is varied to afford a range of copolymers with differing uptake of the hydroxyl monomer into the copolymer.

The copolymers can then be activated by the 1,8-diazabicyclo[5.4.0]-undec-7-ene (DBU) catalysed condensation in dioxane of 2-Vinyl-4,4-dimethylazlactone with the pendant hydroxy functions of the macromolecules. The resultant acrylamide active macromer is isolated by precipitation, and dried in vacuo at 40° C. for 4 hours. The acrylamide functionalised polymer was then dissolved in an excess of water (ca. 50 wt %) 0.3 wt % of the photoinitiator Irgacure 2959 was added, and then the aqueous solution was evaporated down to the appropriate water content, The invention will be further described by reference to preferred embodiments set out in the following examples.

EXAMPLE 1

This Example illustrates the preparation and testing of a composition according to the present invention.

A hydrophilic poly(HBA-co-DMA) copolymer was synthesised by dissolving 2.0013 g 4-hydroxybutyl acrylate monomer (Aldrich Cat. No. 27,557-3) and 6.0755 g N,N-dimethylacrylamide monomer (Aldrich Cat. No. 27,413-5) in 120 ml 1,4-dioxane in a 250 ml round bottom flask equipped with a stirrer bar. 0.123 g (1 mole percent) of azobisisobutyronitrile (AIBN) initiator was added, and the monomer solution was freeze-thaw degassed four times. After reaction at 70° C. for 16 hours, the copolymer was isolated by precipitation into hexane, and was dried in vacuo at 40° C. for 4 hours to yield 6.25 g of a white, powdery polymer.

1.88 g of the polymer was dissolved in 20 ml 1,4 dioxane in a 50 ml round bottom flask equipped with a stirrer bar and nitrogen purge. 70 milligrams of 1,8-diazabicyclo[5.4.0]-undec-7-ene (DBU) (Aldrich Cat. No. 13,900-9) was added, followed by 0.4801 g 2-vinyl-4,4-dimethylazlactone. The reaction mixture was heated at 70° C. for 17 hours and the polymer was isolated by pouring the reaction mixture into excess hexane. The polymer was then dried in vacuo at 40° C. for 4 hours. The acrylamide functionalised polymer was then dissolved in water to give a 30 wt % solution, and 0.3 wt % of the photoinitiator Irgacure 2959 was added. The polymer solution was placed into polypropylene moulds (designed to give a flat polymeric disc of 20.7 mm diameter and 1.0 mm depth) and polymerised for ten minutes under irradiation from a 365 nm UV lamp. After polymerisation was complete, a transparent, rubbery polymer disc was removed from the moulds. The shear modulus of the polymer was measured with a Bohlin controlled stress rheometer (CS-10) and the results are set out in Table 1.

TABLE 1

DMA/Active Hydrogen Copolymers

|  | Mole % Functionalised | Wt % Solids | Viscosity (cSt) | Refractive Index | Polymer Shear Modulus (kPa) |
|---|---|---|---|---|---|
| HBA[1] | 1 | 75.9 | 125,000 | 1.4389 | 0.54 |
|  | 2 | 41.0 | 850 | 1.3901 | 47 |
|  | 3 | 50.1 | 14,600 | 1.4026 | 90.4 |
| NHEA[2] | 1.6 | 65.3 | 117,000 | 1.4161 | 36 |
|  | 1.6 | 49.0 | 16,000 | 1.4014 | 14.5 |

[1]Hydroxyl butyl acrylate
[2]N-hydroxy ethyl acrylamide

EXAMPLES 2 AND 3

These Examples illustrate the preparation and testing of two further compositions according to the present invention.

Example 1 was repeated except that the solids content was reduced to 25% (Example 2) and 20% (Example 3) to produce the results set out in Table 2.

TABLE 2

| Example | Mole % acrylamide functionalised | Formulation solids content (wt %) | Shear modulus (kPa) |
|---|---|---|---|
| 2 | 5 | 25 | 16.0 |
| 3 | 5 | 20 | 2.1 |

The claims defining the invention are as follows:

1. A method of treating presbyopia by removing a patient's lens from the lens capsule bag via an incision in the cornea, injecting into the lens capsule bag a macromonomer of Formula I, and polymerising the macromonomer to a polymer, Formula I being:

$$-[(A)_m - [B\,|\,C]_n]_r-$$

where:
m=an integer≧1
n=an integer≧1
r=an integer≧1

A is a non-reacted moiety resulting from the addition polymerisation of ethylenically unsaturated monomers, B is a moiety resulting from the additional polymerisation of ethylenically unsaturated groups that possess hydroxyl or amino groups bound to the ethylenically unsaturated groups via a carbonyl group and has the following structure:

C has the following structure:

$$\text{CH}_2\text{=C}(R_1)\text{—C(O)—X—W—Z—}$$

where:
R=H, Me
X=O, NH
Z=is optional and is O, NH, NR, S, $CO_2$ where R is $C_1$–$C_8$ alkyl, and
W=is optional and is linear, branched cyclic hydrocarbyl chains, polyether chains or heterochains, linear or cyclic.

2. A method of treating presbyopia as defined in claim 1 wherein the macromonomer is prepared by free radical polymerisation of A and B moieties.

3. A method of treating presbyopia as defined in claim 1 wherein the macromonomer or macromonomer solution has a viscosity at 25° C. in the range 1,000–20,000 cSt and after polymerisation forms a biocompatible polymer having an E modulus in the range 0.01–100 kPa.

4. A method of treating presbyopia as defined in claim 3 wherein the viscosity is in the range 1,000–10,000 cSt.

5. A method of treating presbyopia as defined in claim 1 wherein the biocompatible polymer has an E modulus in the range 0.1–10 kPa.

6. A method of treating presbyopia as defined in claim 1 wherein the polymer formed after polymerisation has an E modulus in the range 0.5–5 kPa.

7. A method of treating presbyopia as defined in claim 1 wherein the macromonomer has a molecular weight in the range 10,000 to 300,000.

8. A method of treating presbyopia as defined in claim 1 in which A is an N,N-dialkyl acrylamide.

9. A method of treating presbyopia as defined in claim 1 wherein A is N,N-dimethyl acrylamide or N,N-diethyl acrylamide.

10. A method of treating presbyopia as defined in claim 1 wherein C is a (meth)acrylate or (meth)acrylamide group.

11. A method of treating presbyopia as defined in claim 1 wherein the macromonomer is formed by reaction of the hydroxy or amino group of B with a compound selected from a group consisting of isocyanatoethylmethacrylate, methacrylate anhydride, acrylate anhydride, active esters of acrylate and methacrylate, azlactones and (meth)acryloyl compounds.

12. A method of treating presbyopia as defined in claim 1 wherein the macromonomer is formed by reaction of the hydroxy or amino group of B with a compound selected from a group consisting of isocyanatoethylmethacrylamide, methacrylamide anhydride, acrylamide anhydride and active esters of acrylamide and methacrylamide.

13. A method of treating presbyopia as defined in claim 1 wherein the macromonomer further comprises styrenic monomeric units.

14. A method of treating presbyopia as defined in claim 1 wherein the molar percentage of A in the macromonomer is at least 95%.

15. A method of treating presbyopia as defined in claim 1 wherein the molar percentage of B in the macromonomer is between 0.5 and 20%.

16. A method of treating presbyopia as defined in claim 1 wherein the molar percentage of B in the macromonomer is between 1 and 3%.

17. A method of treating presbyopia as defined in claim 1 wherein the molar percentage of B–C groups in the macromonomer is between 1 and 5%.

18. A method of treating presbyopia as defined in claim 1 in which W is selected from a group consisting of polyethylene glycol, polyethylene, cyclic and heterocyclic species.

19. A method of treating presbyopia as defined in claim 1 in which W is one or more of hydroxyalkylacrylate, hydroxyalkylacrylamide, aminoalkylacrylate or aminoalkylacrylamide.

20. A method of treating presbyopia as defined in claim 1 in which B is one or more of hydroxybutylacrylamide or N-hydroxyethylacrylamide.

* * * * *